(12) United States Patent
Bacik (10) Patent No.: US 7,981,361 B2
(45) Date of Patent: Jul. 19, 2011

(54) CIRCULATION AND DISPOSAL DEVICE FOR MULTI-PURPOSE STERILIZATION CHAMBERS AND WASHING CHAMBERS

(75) Inventor: Michael A. Bacik, Fairview, PA (US)

(73) Assignee: American Sterilizer Company, Mentor, OH (US)

( * ) Notice: Subject to any disclaimer, the term of this patent is extended or adjusted under 35 U.S.C. 154(b) by 0 days.

(21) Appl. No.: 12/641,470

(22) Filed: Dec. 18, 2009

(65) Prior Publication Data

US 2010/0166602 A1 Jul. 1, 2010

Related U.S. Application Data

(60) Provisional application No. 61/141,858, filed on Dec. 31, 2008.

(51) Int. Cl.
*A61L 2/00* (2006.01)
*B08B 3/00* (2006.01)
(52) U.S. Cl. .......................................... 422/28; 134/111
(58) Field of Classification Search .................... 422/28; 134/111
See application file for complete search history.

(56) References Cited

U.S. PATENT DOCUMENTS

| | | | | |
|---|---|---|---|---|
| 2,792,908 A * | 5/1957 | Glanzer | .......................... | 96/398 |
| 5,472,004 A * | 12/1995 | Gilliard | ......................... | 134/111 |
| 7,135,142 B2 * | 11/2006 | Burke et al. | ..................... | 422/28 |
| 7,559,122 B2 * | 7/2009 | Schatzmann et al. | ........... | 19/113 |
| 7,811,534 B2 * | 10/2010 | Hultholm et al. | ............... | 423/27 |
| 2005/0011356 A1 | 1/2005 | Laiti | ................................ | 95/273 |
| 2005/0084431 A1 | 4/2005 | Hill et al. | ..................... | 422/305 |
| 2008/0279722 A1 | 11/2008 | Bacik et al. | .................... | 422/29 |

* cited by examiner

*Primary Examiner* — Robert J Warden
(74) *Attorney, Agent, or Firm* — Kusner & Jaffe; Michael A. Centanni (57) ABSTRACT

The present invention provides an apparatus for circulating a carrier gas containing a chemical deactivating vapor or gas in a chamber. The apparatus includes a housing defining a flow path therethrough. The housing has an inlet end and an outlet end. A blower is provided for conveying a carrier gas containing a chemical deactivating vapor or gas along the flow path. A filter that includes a filter element is provided. The filter is movable between a first position and a second position, wherein the filter element is fluidly isolated from the flow path when the filter is in the first position, and the filter element is disposed in the flow path when the filter is in the second position. An actuator is provided for moving the filter between the first position and the second position.

19 Claims, 7 Drawing Sheets

CIRCULATION AND DISPOSAL DEVICE FOR MULTI-PURPOSE STERILIZATION CHAMBERS AND WASHING CHAMBERS

RELATED APPLICATIONS

This application claims the benefit of U.S. Provisional Application No. 61/141,858, filed Dec. 31, 2008, which is fully incorporated herein by reference.

FIELD OF THE INVENTION

The present invention relates generally to decontamination or sterilization systems and, more particularly, to a device for circulating and destroying a chemical deactivating vapor or gas in a decontamination or sterilization chamber.

BACKGROUND OF THE INVENTION

Medical, dental, pharmaceutical, veterinary or mortuary instruments and devices that are exposed to blood or other body fluids require thorough cleaning and microbial deactivation between each use. The instruments and devices typically are placed into a chamber of a conventional washer system where they are exposed to a washing fluid. The washing fluid is circulated throughout the chamber to remove large debris and other contamination from the instruments and device. Conventional washer systems typically have dedicated racks, shelves or carts that hold the instruments and devices being deactivated. The racks, shelves or carts are dimensioned to be received into a chamber within the system.

Following a washing cycle, the instruments and devices are placed into a decontamination or a sterilization system wherein they are exposed to a chemical deactivating vapor or gas. The chemical deactivating vapor or gas deactivates microbial organisms on the instruments and devices.

Combination washer/decontamination or washer/sterilization systems have recently been developed wherein the instruments and devices are exposed to a washing fluid and a chemical deactivating vapor or gas in the same chamber. In some instances, attempts have been made to make combination washer/decontaminators or washer/sterilizers from existing washer systems. Such combination systems may be formed by fluidly connecting a conventional chemical deactivating vapor or gas delivery system to the chamber of an existing washing system. Conventional delivery systems typically include external blowers, pumps or fans that are used to circulate a carrier gas containing a chemical deactivating vapor or gas through the chamber. The delivery system may also include means for generating and destroying the chemical deactivating vapor or gas.

After the instruments and devices are washed with the washing fluid, the combination washer/decontamination or washer/sterilization system initiates a decontamination or a sterilization cycle. During the cycle, a carrier gas containing a chemical deactivating vapor or gas is introduced into and circulated throughout the chamber. It is important that the chemical deactivating vapor or gas be properly distributed throughout the chamber to insure deactivation of the instruments and devices in the chamber.

After a predetermined period of time, the chemical deactivating vapor or gas is removed from the carrier gas by circulating the carrier gas and the chemical deactivating vapor or gas through a catalyst or filter external to the chamber. The catalyst or filter is comprised of a material that is chemically active with respect to molecules of the chemical deactivating vapor or gas as, by way of example and not limitation, by catalysis, physical forces, electrical forces, or chemical reaction. Adequate mixing of the carrier gas and the chemical deactivating vapor or gas in the chamber increases the likelihood that the chemical deactivating vapor or gas in the chamber will be conveyed through the catalyst or filter.

A problem with using existing washer systems to form a combination washer/decontamination or washer/sterilization system is that the washer systems are not designed for optimal mixing of a carrier gas and a chemical deactivating vapor or gas in the chamber. In addition external blowers, pumps, or fans are usually inadequate to effectively circulate the carrier gas and the chemical deactivating vapor or gas throughout the chamber of an existing washer system.

The present invention provides a portable device that may be placed into a chamber to facilitate circulation and disposal of a chemical deactivating vapor or gas in a carrier gas.

SUMMARY OF THE INVENTION

In accordance with one embodiment of the present invention, there is provided an apparatus for circulating a carrier gas containing a chemical deactivating vapor or gas in a chamber. The apparatus includes a housing defining a flow path therethrough. The housing has an inlet end and an outlet end. A blower is provided for conveying a carrier gas containing a chemical deactivating vapor or gas along the flow path. A filter that includes a filter element is provided. The filter is movable between a first position and a second position, wherein the filter element is fluidly isolated from the flow path when the filter is in the first position, and the filter element is disposed in the flow path when the filter is in the second position. An actuator is provided for moving the filter between the first position and the second position.

In accordance with another embodiment of the present invention, there is provided a system for deactivating biocontamination on devices. The system includes a chamber. A rack is provided for holding items to be deactivated. The rack is disposed within the chamber. At least one circulation and disposal device is disposed on the rack. The at least one circulation and disposal device includes a housing that defines a flow path therethrough. The housing has an inlet end and an outlet end. A fan is provided for conveying a carrier gas containing a chemical deactivating vapor or gas along the flow path. A filter is mounted to move within the housing. The filter includes a filter element. An actuator is provided for moving the filter between a first position and a second position, wherein the filter element in the filter is fluidly isolated from the flow path when the filter is in the first position, and the filter element is disposed in the flow path when the filter is in the second position.

In accordance with yet another embodiment of the present invention, there is provided a method for circulating a carrier gas in a system. The method includes the steps of: a) locating a filter to a first position wherein a filter element in the filter is fluidly isolated from a flow path defined by the housing when a system is in a chemical deactivating vapor or gas circulation phase; b) conveying a carrier gas containing a chemical deactivating vapor or gas that deactivates microbial contamination along the flow path; and c) locating the filter to a second position wherein the filter element is disposed in the flow path when the system is in an aeration phase.

One advantage of the present invention is an apparatus for circulating a carrier gas containing a chemical deactivating vapor or gas through a chamber.

Another advantage of the present invention is an apparatus for circulating a carrier gas containing a chemical deactivating vapor or gas, as described above, wherein the apparatus is placed in a decontamination or sterilization chamber to facilitate the circulation of the carrier gas and chemical deactivating vapor or gas therein.

Another advantage of the present invention is an apparatus for circulating a carrier gas containing a chemical deactivating vapor or gas through a chamber, wherein a filter/catalyst element may be selectively placed in a flow path through the apparatus.

Yet another advantage of the present invention is an apparatus for circulating a carrier gas containing a chemical deactivating vapor or gas through a chamber during a decontamination or sterilization phase.

Yet another advantage of the present invention is an apparatus for circulating a carrier gas containing a chemical deactivating vapor or gas through a chamber, wherein the chemical deactivating vapor or gas is destroyed in the apparatus during an aeration phase.

Another advantage of the present invention is an apparatus for circulating a carrier gas containing a chemical deactivating vapor or gas, as described above, wherein the apparatus is placed in the chamber of a decontamination or a sterilization system to facilitate the distribution of a chemical deactivating vapor or gas in the chamber.

Another advantage of the present invention is an apparatus for circulating a carrier gas containing a chemical deactivating vapor or gas, as described above, wherein the apparatus is placed in the chamber of a decontamination or a sterilization system to facilitate the removal of a chemical deactivating vapor or gas from the chamber.

Another advantage of the present invention is an apparatus for circulating a carrier gas containing a chemical deactivating vapor or gas, as described above, wherein the apparatus is added to an existing system to facilitate the circulation of the carrier gas and the chemical deactivating vapor or gas therein.

Yet another advantage of the present invention is an apparatus for circulating a carrier gas containing a chemical deactivating vapor or gas, as described above, wherein the apparatus is attachable to an existing shelf of a rack in a chamber.

These and other advantages will become apparent from the following description of a preferred embodiment taken together with the accompanying drawings and the appended claims.

BRIEF DESCRIPTION OF THE DRAWINGS

The invention may take physical form in certain parts and arrangement of parts, a preferred embodiment of which will be described in detail in the specification and illustrated in the accompanying drawings which form a part hereof, and wherein.

DETAILED DESCRIPTION OF PREFERRED EMBODIMENT

Figure 1:
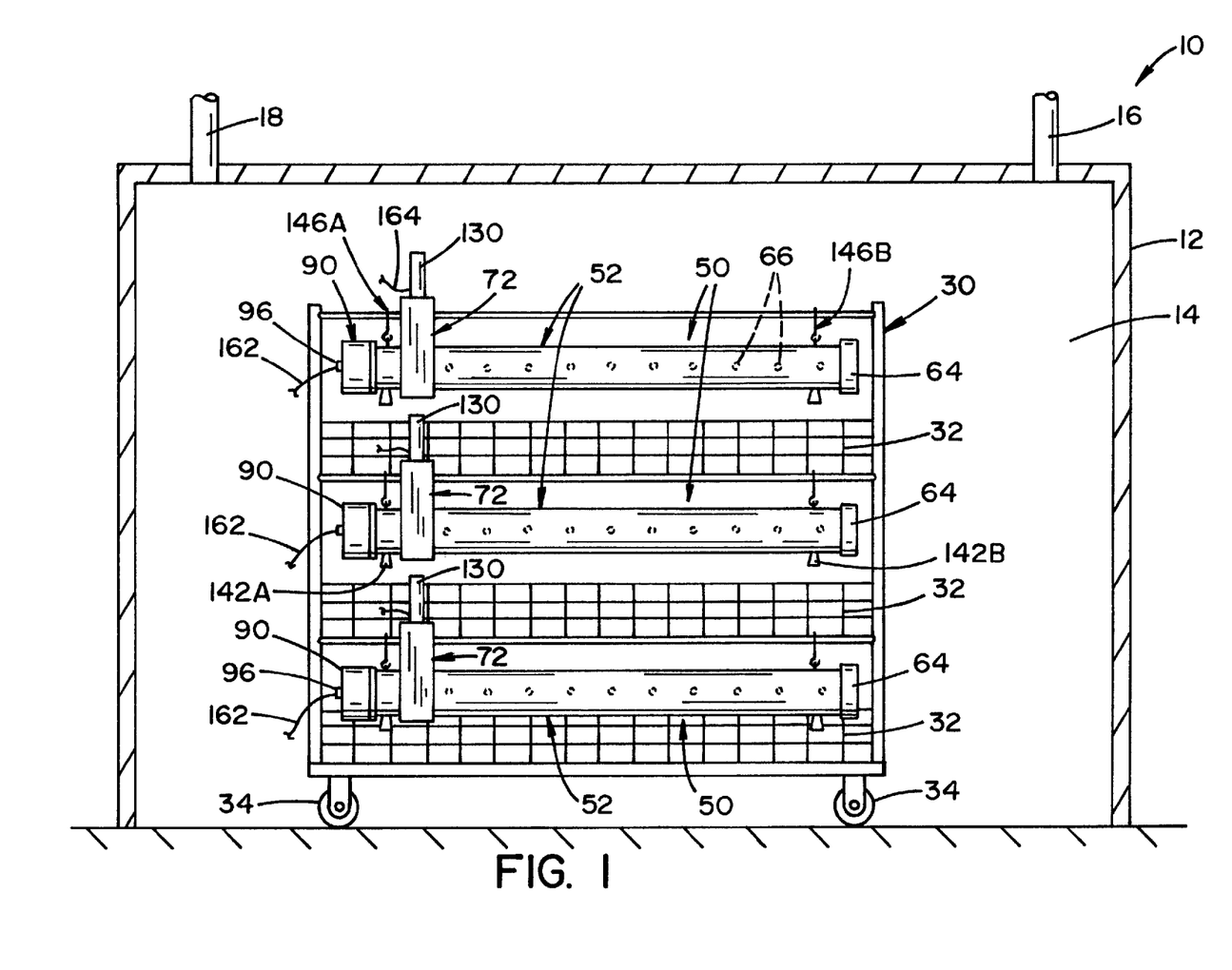
FIG. 1 is a side, sectional view of a combination washer/sterilization system showing a rack disposed in a chamber of the system, and further showing a plurality of circulation and disposal devices according to the present invention that are attached to the rack.

Referring now to the drawings wherein the showings are for the purpose of illustrating a preferred embodiment of the invention only and not for the purpose of limiting the same, FIG. 1, shows a view of a combination washer/sterilization system 10. System 10 will be described below with reference to a washer/sterilization system. However, it is contemplated that system 10 may also be a washer/decontamination system that includes components similar to the components of a washer/sterilization system.

Figure 2:
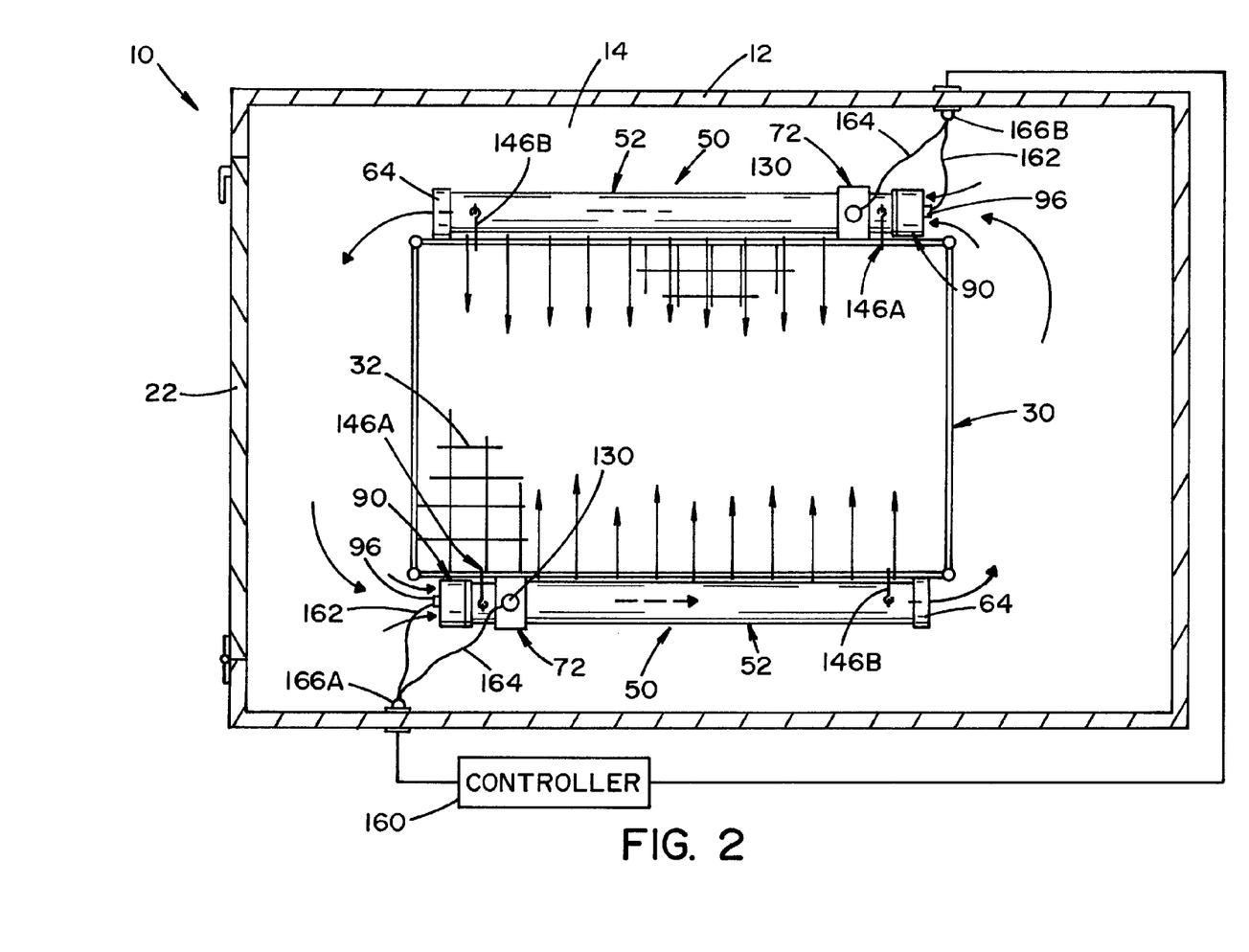
FIG. 2 is a top, sectional view of the combination washer/sterilization system shown in FIG. 1.

System 10 is generally comprised of a housing 12 that defines an internal chamber 14. An inlet 16 and an outlet 18 extend through housing 12 to fluidly communicate with internal chamber 14 in system 10. Inlet 16 and outlet 18 are connected to a conventional chemical deactivating vapor or gas delivery system (not shown). The delivery system includes means for conveying a carrier gas containing a chemical deactivating vapor or gas to internal chamber 14. It is contemplated that the delivery system may also include means for generating and destroying the chemical deactivating vapor or gas. For example, the delivery system may be a conventional vaporized hydrogen peroxide (VHP) delivery system that includes a blower for conveying a carrier gas, a vaporizer for generating VHP that is introduced into the carrier gas and a destroyer for destroying VHP. As best seen in FIG. 2, housing 12 includes a door 22 that allows access to internal chamber 14.

As seen in FIG. 1, system 10 contains one or more racks 30. Rack 30 includes a plurality of shelves 32 that holds instruments and/or devices to be deactivated. Rack 30 includes a plurality of wheels 34 to facilitate easy movement of rack 30 into and out of internal chamber 14 in system 10.

In the embodiment shown, a plurality of circulation and disposal devices 50, according to the present invention, is disposed on rack 30. Each circulation and disposal device 50 is essentially identical and only one device 50 shall be described in detail.

Figure 3A:
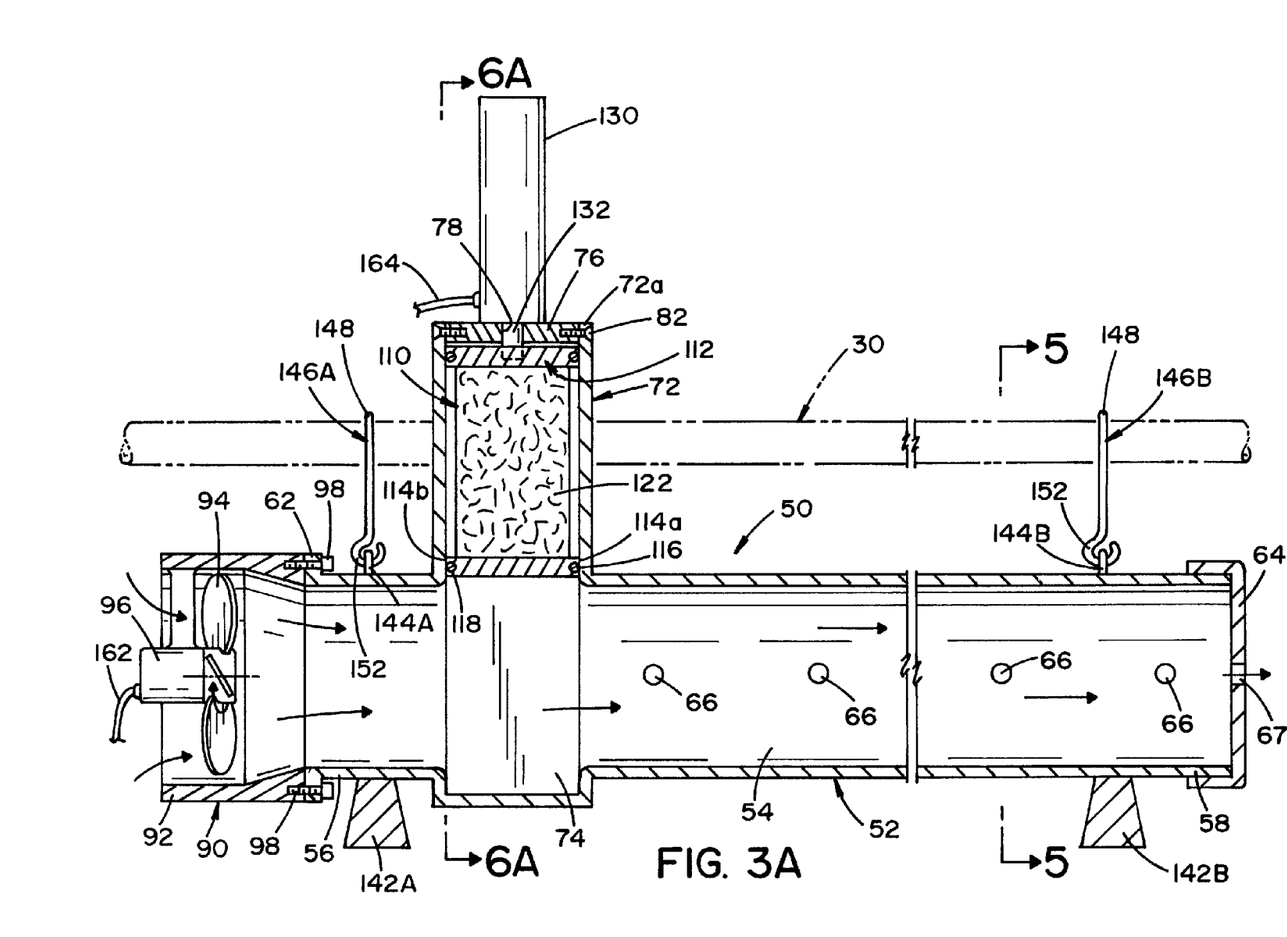
FIG. 3A is an enlarged, sectional side view of a circulation and disposal device according to the present invention, showing the device in a first operating position.

As best seen in FIG. 3A, each circulation and disposal device 50 includes an elongated tubular body 52 that defines an internal passage 54 therethrough. In the embodiment shown, tubular body 52 is cylindrical in shape. Tubular body 52 has a first end 56 and a second end 58. An outwardly extending flange 62 is formed on first end 56 of tubular body 52. Flange 62 includes a plurality of holes extending axially therethrough. A cap 64 is disposed on second end 58 of tubular body 52. A nozzle 67 extends through cap 64. A series of spaced-apart nozzles 66 extend through tubular body 52 at discrete locations along tubular body 52.

A blower assembly 90 is provided for conveying the carrier gas and the chemical deactivating vapor or gas through internal passage 54 in tubular body 52. Blower assembly 90 is attached to flange 62 of tubular body 52 by a plurality of bolts 98. Blower assembly 90 includes a housing 92 that is dimensioned to receive a fan 94 and a motor 96 therein. Motor 96 is attached to fan 94 and is operable to cause fan 94 to rotate. Fan 94 is operable to rotate within housing 92 to draw the carrier gas and the chemical deactivating vapor or gas into housing 92.

Tubular body 52 includes a housing 72 near first end 56 in tubular body 52. In the embodiment shown, housing 72 is rectangular in shape. Housing 72 has an open end 72a and defines a cavity 74 therein. Cavity 74 in housing 72 communicates with internal passage 54 in tubular body 52. A plate 76 is disposed in open end 72a in housing 72. Plate 76 includes a hole 78 extending therethrough. Plate 76 is secured in open end 72a in housing 72 by a plurality of screws 82.

A filter 110 is provided to move within housing 72 in device 50. Filter 110 includes an outer support frame 112 that has two end faces 114a, 114b. In the embodiment shown, outer support frame 112 is rectangular in shape. A first o-ring 116 is disposed in an o-ring groove formed in end face 114a. A second o-ring 118 is disposed in an o-ring groove formed in end face 114b. O-rings 116, 118 are dimensioned to sealingly engage an inner surface of housing 72. Outer support frame 112 is dimensioned to receive a filter/catalyst element 122 therein. Filter/catalyst element 122 is made from a material that is chemically active (e.g., destructive or reactive) with respect to molecules of the chemical deactivating vapor or gas to be used in system 10. The interaction of filter/catalyst element 122 with the molecules of the chemical deactivating vapor or gas may occur, by way of example and not limitation, by catalysis, physical forces, electrical forces, or chemical reaction. For example, for systems wherein the chemical deactivating vapor or gas is vaporized hydrogen peroxide (VHP), filter/catalyst element 122 may be formed of glass frits, precious metals, copper, silver or a transition metal including, but not limited to, platinum and palladium and transition metal oxides including, but not limited to, oxides of manganese such as, for example, manganese dioxide that are catalytic to the destruction of VHP. The catalytic destruction of VHP results in the formation of oxygen and water. In other systems, wherein the chemical deactivating vapor or gas is ozone, filter/catalyst element 122 may be formed of carbon or a carbon-containing material. The reaction of carbon with ozone results in the formation of carbon dioxide and carbon monoxide.

Figure 3B:
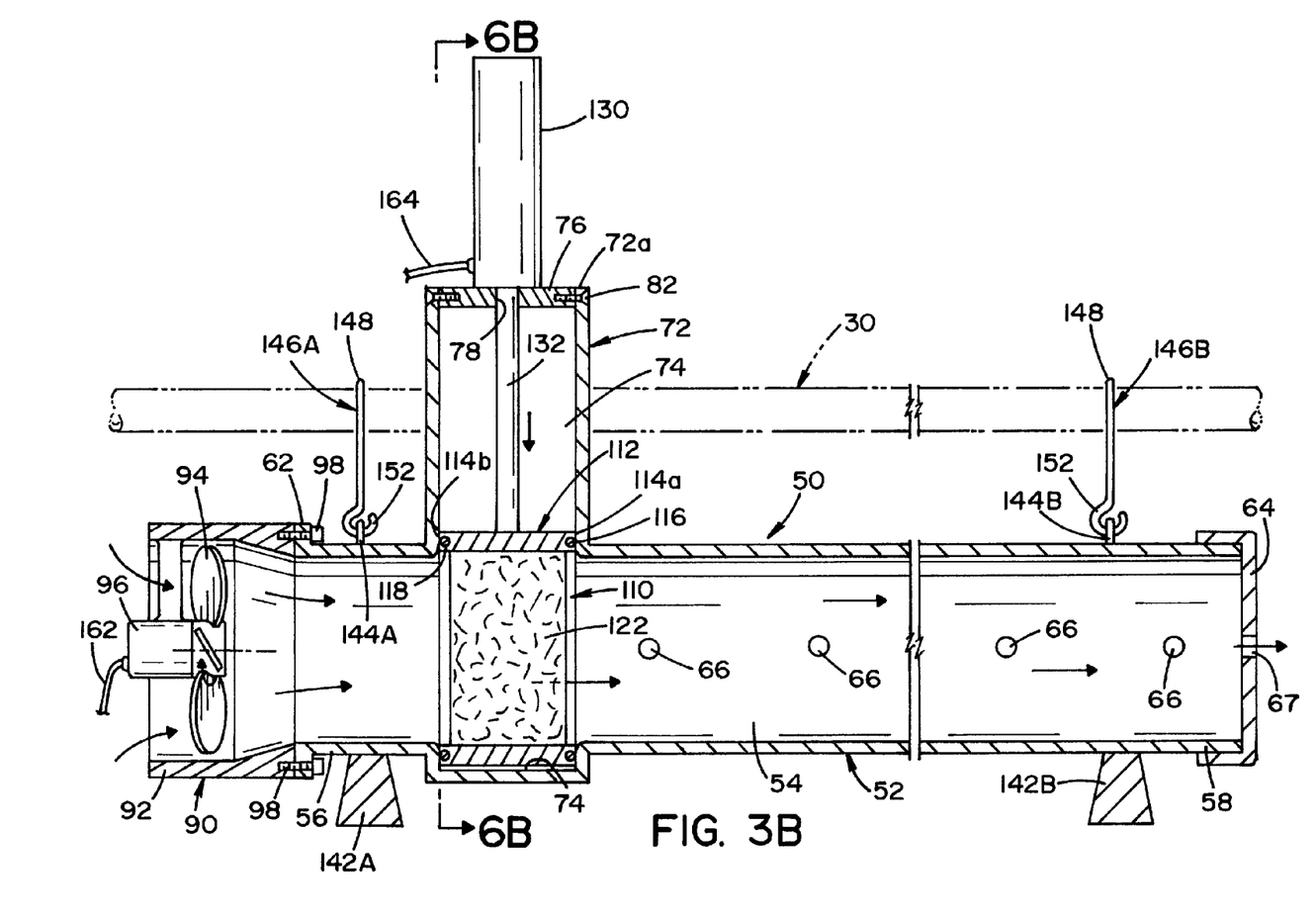
FIG. 3B is an enlarged, sectional side view of the circulation and disposal device shown in FIG. 3A, showing the device in a second operating position.
Figure 4:
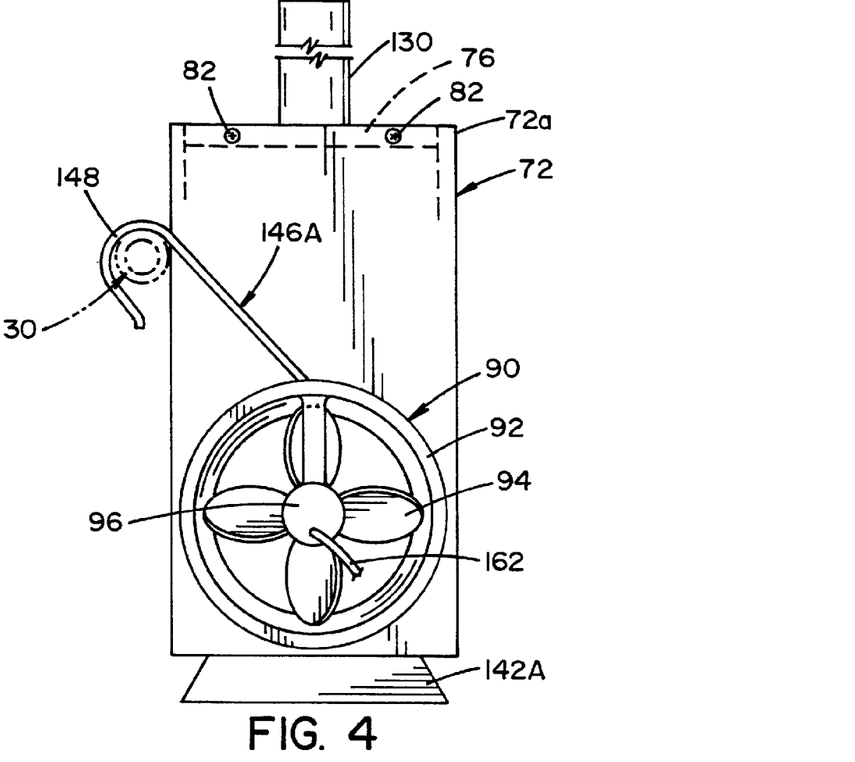
FIG. 4 is an enlarged view of an inlet end of the circulation and disposal device shown in FIG. 3A.
Figure 5:
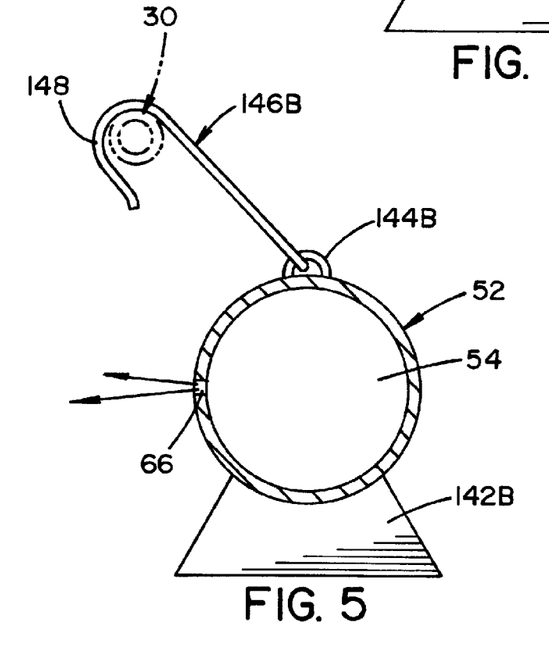
FIG. 5 is an enlarged, sectional view taken along lines 5-5 in FIG. 3A.
Figure 6A:
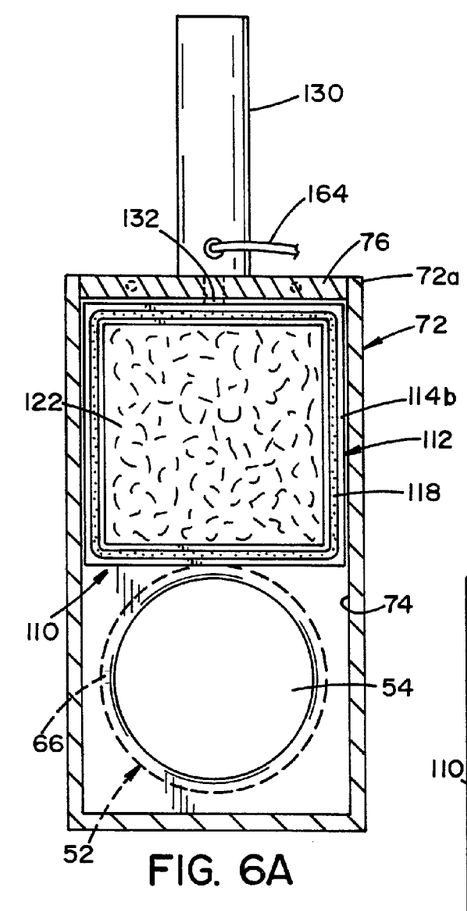
FIG. 6A is an enlarged, sectional view taken along lines 6A-6A in FIG. 3A.
Figure 6B:
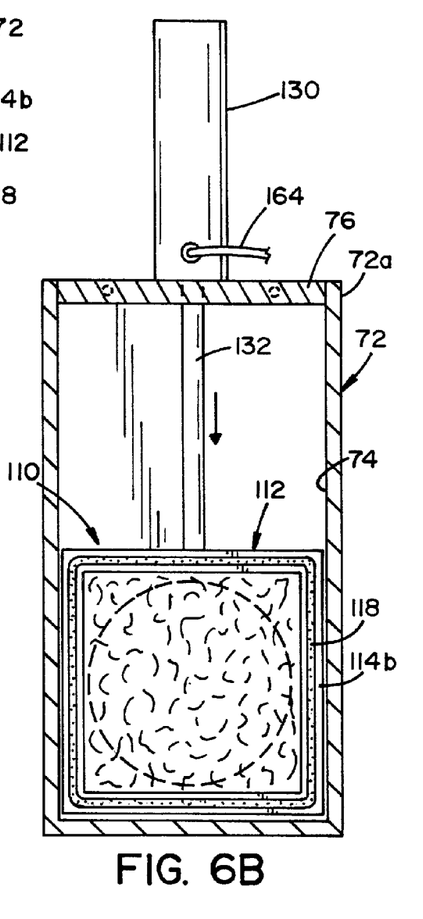
FIG. 6B is an enlarged, sectional view taken along lines 6B-6B in FIG. 3B.

Filter 110 is dimensioned to move within cavity 74 in device 50 between a first position, shown in FIGS. 3A and 6A, and a second position, shown in FIGS. 3B and 6B. When filter 110 is located in the first position, filter/catalyst element 122 is fluidly isolated from internal passage 54 in device 50. When filter 110 is located in the second position, filter/catalyst element 122 fluidly communicates with internal passage 54 in device 50.

An actuator assembly 130 is attached to plate 76 in device 50. Actuator assembly 130 includes an actuating rod 132 that extends through hole 78 in plate 76. A distal end of actuating rod 132 is secured to support frame 112 of filter 110. Actuator assembly 130 is operable to move actuating rod 132 such that filter 110 moves between a first position and a second position. In the first position, actuating rod 132 positions filter 110 such that filter/catalyst element 122 is fluidly isolated from internal passage 54 in device 50. In the second position, actuating rod 132 extends such that filter/catalyst element 122 fluidly communicates with internal passage 54 in device 50. In the embodiment shown, actuator assembly 130 is an electrically actuated device, such as an electrically actuated solenoid valve or an electric motor. It is also contemplated that actuator assembly 130 may also be a pneumatically actuated device, such as a pneumatically actuated piston.

As shown in FIG. 3A, a pair of support legs 142A, 142B extend downwardly from tubular body 52 near first end 56 and second end 58, respectively. In the embodiment shown, support legs 142A, 142B are trapezoidal in shape. A pair of mounting rings 144A, 144B are attached to a top of tubular body 52 near first end 56 and second end 58, respectively.

Hanger elements 146A, 146B are provided for securing circulation and disposal device 50 to rack 30, as best seen in FIGS. 3A-3B. Hanger elements 146A, 146B are identical and as such, only hanger element 146A will be described in detail. Hanger element 146A is a rod shaped element with a first hook portion 148 and a second hook portion 152. First hook portion 148 is dimensioned to secure around a portion of rack 30. Second hook portion 152 is dimensioned to attach to mounting ring 144A on circulation and disposal device 50.

A controller 160, shown in FIG. 2, is provided for controlling the operation of circulation and disposal device 50. Preferably, controller 160 is connected to a system controller (not shown) to operate devices 50 in conjunction with the operation of system 10. A lead 162 connects controller 160 to motor 96 in blower assembly 90 thereby allowing controller 160 to control the operation of blower assembly 90. A lead 164 connects controller 160 to actuator assembly 130 thereby allowing controller 160 to control the actuation of actuator assembly 130. A pair of fluid tight connectors 166A, 166B are disposed in housing 12 of system 10. Fluid tight connectors 166A, 166B allow leads 162, 164 to pass through housing 12 while maintaining internal chamber 14 in system 10 fluidly isolated from an exterior of system 10.

Referring now to the operation of the present invention, rack 30, with a plurality of circulation and disposal devices 50 disposed thereon, is moved into chamber 14 of system 10, as shown in FIG. 1. It is contemplated that devices 50 may also be mounted on the floor in system 10 using support legs 142A, 142B. In the embodiment shown, circulation and disposal devices 50 are attached to rack 30 by hanger elements 146A, 146B. A typical decontamination or sterilization cycle of system 10 includes a chemical deactivating vapor or gas introduction phase, a chemical deactivating vapor or gas circulation phase and an aeration phase.

During the chemical deactivating vapor or gas introduction phase, a carrier gas that contains a chemical deactivating vapor or gas is introduced into internal chamber 14 in system 10 through inlet 16 by a chemical deactivating vapor or gas delivery system (not shown). If filter 110 is located in the second position when the chemical deactivating vapor or gas introduction phase commences, then filter 110 is moved to the first position. Controller 160 causes actuating rod 132 of actuation assembly 130 to retract thereby placing filter 110 in the first position, as shown in FIG. 3A. In this position, i.e., the first position, filter/catalyst element 122 is fluidly isolated from internal passage 54 in device 50. Controller 160 also energizes motor 96 in blower assembly 90 thereby causing fan 94 to rotate and draw the carrier gas, with a chemical deactivating vapor or gas therein, into internal passage 54 in device 50. The carrier gas and the chemical deactivating vapor or gas exit device 50 through nozzles 66, 67, as illustrated in FIG. 3B. In this respect, the carrier gas and chemical deactivating vapor or gas exiting device 50 through nozzles 66, 67 form jets of high velocity flow. These jets of high velocity flow may induce turbulent flow of the carrier gas and the chemical deactivating vapor or gas within chamber 14 and over the instruments and devices in rack 30. In this regard, the jets of high velocity flow may facilitate the circulation of the carrier gas and the chemical deactivating vapor or gas throughout chamber 14.

The chemical deactivating vapor or gas introduction phase continues until a concentration of the chemical deactivating vapor or gas has reached a predetermined level. Once the predetermined level is reached, a chemical deactivating vapor or gas circulation phase begins.

During the chemical deactivating vapor or gas circulation phase, the concentration of the chemical deactivating vapor or gas in internal chamber 14 is monitored to assure that a predetermined concentration is reached and maintained. Controller 160 maintains blower assembly 90 in the "ON" position to facilitate distribution of the carrier gas and the chemical deactivating vapor or gas throughout internal chamber 14. After a predetermined period of time, the chemical deactivating vapor or gas circulation phase ends and an aeration phase is initiated.

During the aeration phase, the chemical deactivating vapor or gas in internal chamber 14 is destroyed. As stated above, the chemical deactivating vapor or gas delivery system attached to system 10 may include a destroyer for destroying the chemical deactivating vapor or gas. The carrier gas in internal chamber 14 is drawn through outlet 18 into the destroyer in the chemical deactivating vapor or gas delivery system. The present invention provides a device 50 that facilitates the destruction of the chemical deactivating vapor or gas.

During operation, controller 160 causes actuating assembly 130 to extend actuating rod 132 thereby moving filter 110 from the first position, as shown in FIGS. 3A and 6A, to the second position, as shown in FIGS. 3B and 6B. As a result, filter/catalyst element 122 now fluidly communicates with internal passage 54 in device 50. As stated above, filter/catalyst element 122 is made of a material that is chemically active (e.g., destructive or reactive) with respect to molecules of the chemical deactivating vapor or gas. As blower assembly 90 conveys the carrier gas containing a chemical deactivating vapor or gas therein through filter/catalyst element 122, the chemical deactivating vapor or gas reacts with or is destroyed by filter/catalyst element 122. In this respect, the chemical deactivating vapor or gas is removed from the carrier gas. The carrier gas then exits out of device 50 through nozzles 66, 67, as illustrated in FIG. 3B.

The present invention thus provides a device for efficiently removing a chemical deactivating vapor or gas from a carrier gas in an internal chamber 14 of a system 10.

As described above, the present invention also provides a device that facilitates that circulation of a carrier gas and a chemical deactivating vapor or gas within a chamber of a decontamination or a sterilization system during a chemical deactivating vapor or gas circulation phase. In addition, the present invention facilitates the destruction of the chemical deactivating vapor or gas during an aeration phase.

Figure 7A:
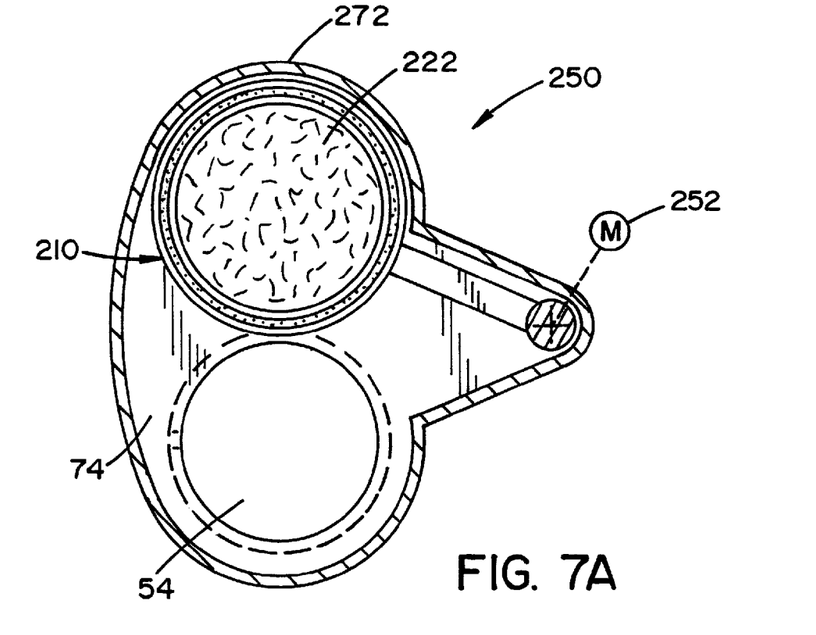
FIG. 7A is a sectional view of a circulation and disposal device according to another embodiment of the present invention showing the device in a first operating position.
Figure 7B:
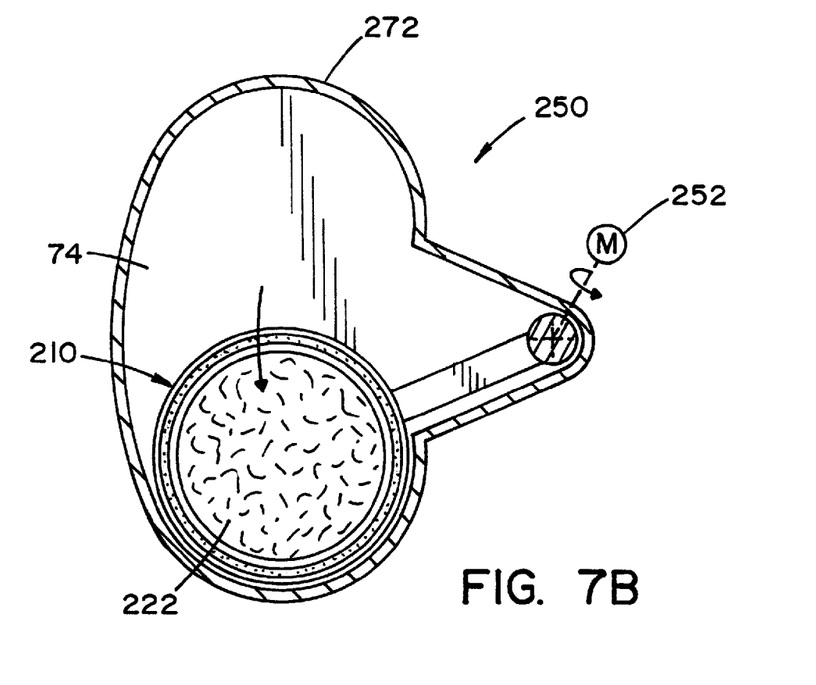
FIG. 7B is a sectional view of a circulation and disposal device shown in FIG. 7A, showing the device in a second operating position.

Referring to FIGS. 7A and 7B, circulation and disposal device 250, illustrating an alternate embodiment of the present invention, is shown. Device 250 includes an obround housing 272 that is dimensioned to receive a filter 210 therein. Housing 272 is dimensioned to allow filter 210 to move in an arc-shaped path therein. In the embodiment shown, filter 210 is a cylindrical shaped element that moves between a first position, seen in FIG. 7A, and a second position, seen in FIG. 7B.

When filter 210 is in the first position, a filter/catalyst element 222, therein, is fluidly isolated from a flow path through circulation disposal device 250. When filter 210 is in the second position, filter/catalyst element 222 fluidly communicates with the flow path through circulation disposal device 250. Circulation and disposal device 250 includes a motor 252 that is operable to rotate filter 210 between the first position and the second position.

The foregoing description is a specific embodiment of the present invention. It should be appreciated that this embodiment is described for purposes of illustration only, and that numerous alterations and modifications may be practiced by those skilled in the art without departing from the spirit and scope of the invention. It is intended that all such modifications and alterations be included insofar as they come within the scope of the invention as claimed or the equivalents thereof.

Having described the invention, the following is claimed:

1. An apparatus for circulating a carrier gas containing a chemical vapor or gas in a chamber, said apparatus comprised of:
    a housing defining a flow path therethrough, said housing having an inlet end and an outlet end;
    a blower for conveying a carrier gas containing a chemical vapor or gas along said flow path;
    a filter including a filter element, said filter is movable between a first position and a second position, wherein said filter element is fluidly isolated from said flow path when said filter is in said first position, and said filter element is disposed in said flow path when said filter is in said second position; and
    an actuator for moving said filter between said first position and said second position.

2. An apparatus as defined in claim 1, wherein said outlet comprises a plurality of openings disposed in said housing.

3. An apparatus as defined in claim 1, wherein said housing includes at least one mounting ring for mounting said housing to a rack.

4. An apparatus as defined in claim 1, wherein said housing includes at least one support leg for supporting said housing on a floor.

5. An apparatus as defined in claim 1, wherein said filter element includes a material chemically active with respect to molecules of said chemical vapor or gas.

6. An apparatus as defined in claim 5, wherein said material interacts with molecules of said chemical vapor or gas by catalysis, physical force, electrical force or chemical reaction.

7. An apparatus as defined in claim 5, wherein said material is glass frits, precious metals, copper, silver, a transition metal or a transition metal oxide.

8. An apparatus as defined in claim 7, wherein said transition metal is platinum or palladium.

9. An apparatus as defined in claim 7, wherein said transition metal oxide is an oxide of manganese.

10. A system for circulating a carrier gas containing a chemical vapor or gas, said system comprising:
    a chamber;
    a rack for holding items, said rack disposed within said chamber; and
    at least one circulation and disposal device disposed on said rack, said at least one circulation and disposal device comprised of:
        a housing defining a flow path therethrough, said housing having an inlet end and an outlet end;
        a fan for conveying a carrier gas containing a chemical vapor or gas along said flow path;
        a filter mounted to move within said housing, said filter including a filter element; and
        an actuator for moving said filter between a first position and a second position, wherein said filter element in said filter is fluidly isolated from said flow path when said filter is in said first position, and said filter element is disposed in said flow path when said filter is in said second position.

11. A system as defined in claim 10, wherein said outlet end of said at least one circulation and disposal device comprises a plurality of openings disposed in said housing.

12. A system as defined in claim 10, wherein said housing of said at least one circulation and disposal device includes at least one mounting ring for mounting said housing to a rack.

13. A system as defined in claim 10, wherein said housing of said at least one circulation and disposal device includes at least one support leg for supporting said housing on a floor of said chamber.

14. A system as defined in claim 10, wherein said filter element of said at least one circulation and disposal device includes a material chemically active with respect to molecules of said chemical vapor or gas.

15. A system as defined in claim 14, wherein said material interacts with molecules of said chemical vapor or gas by catalysis, physical force, electrical force or chemical reaction.

16. A system as defined in claim 14, wherein said material is glass fits, precious metals, copper, silver, a transition metal or a transition metal oxide.

17. A system as defined in claim 16, wherein said transition metal is platinum or palladium.

18. A system as defined in claim 16, wherein said transition metal oxide is an oxide of manganese.

19. A method for circulating a carrier gas containing a vapor or gas in a system, said method comprising the steps of:
   a) locating a filter to a first position wherein a filter element in said filter is fluidly isolated from a flow path defined by said housing, when a system is in a chemical vapor or gas circulation phase;
   b) conveying a carrier gas containing a chemical vapor or gas along said flow path; and
   c) locating said filter to a second position, wherein said filter element is disposed in said flow path, when said system is in an aeration phase.

* * * * *